US00PP36863P2

(12) United States Plant Patent
Clark et al.

(10) Patent No.: US PP36,863 P2
(45) Date of Patent: Jul. 29, 2025

(54) GRAPEVINE PLANT NAMED 'MN 1369'

(50) Latin Name: ***Vitis* spp. hybrid**
Varietal Denomination: MN 1369

(71) Applicant: REGENTS OF THE UNIVERSITY OF MINNESOTA, Minneapolis, MN (US)

(72) Inventors: Matthew Clark, Hopkins, MN (US); Jennifer Thull, Excelsior, MN (US); John Richard Thull, Excelsior, MN (US)

(73) Assignee: REGENTS OF THE UNIVERSITY OF MINNESOTA, Minneapolis, MN (US)

( * ) Notice: Subject to any disclaimer, the term of this patent is extended or adjusted under 35 U.S.C. 154(b) by 0 days.

(21) Appl. No.: 19/025,516

(22) Filed: Jan. 16, 2025

Related U.S. Application Data

(60) Provisional application No. 63/627,786, filed on Jan. 31, 2024.

(51) Int. Cl.
*A01H 5/08* (2018.01)
*A01H 6/88* (2018.01)

(52) U.S. Cl.
USPC ..... Plt./207

(58) Field of Classification Search
USPC ..... Plt./207
CPC ..... A01H 5/08; A01H 5/00; A01H 6/88
See application file for complete search history.

*Primary Examiner* — June Hwu
(74) *Attorney, Agent, or Firm* — Penny J. Aguirre

(57) ABSTRACT

The invention is a new and distinct variety of grapevine plant named 'MN 1369' that is characterized by its seedless berries (small seed traces only), its berries that are medium in size, its berries with a pleasant tropical fruit flavor, its loose berry clusters, its production of berries on secondary buds, and its berries with adherent skin unless overripe.

2 Drawing Sheets

Botanical classification: *Vitis* spp. hybrid.
Variety denomination: 'MN 1369'.

BACKGROUND OF THE INVENTION

The present invention relates to a new and distinct cultivar of grape plant botanically known as *Vitis* spp. hybrid 'MN 1369', referred to hereafter by its cultivar name, 'MN 1369'. 'MN 1369' is a new cultivar of grape for use as a table grape.

'MN 1369' resulted from an ongoing research program in Excelsior, Minnesota with the objective of the breeding program to develop new cultivars of cold-hardy grapes suitable for table grape production in the Eastern United States.

'MN 1369' originated from a cross made in June of 2007 between the *Vitis* spp. hybrid cultivar designated as 'MN 1104' (not patented) as the female parent and 'Petite Jewel' (not patented) as the male parent. 'MN 1369' was selected as a single unique plant from the seedlings that derived from the above cross in August of 2015.

Asexual propagation of the new cultivar was first accomplished by hardwood stem cuttings in February of 2016 by one of the Inventors in Excelsior, Minnesota. Asexual propagation of the new cultivar by hardwood stem cuttings and tissue culture using meristamic tissue has determined that the characteristics are stable and true to type in successive generations.

SUMMARY OF THE INVENTION

The following traits have been repeatedly observed and represent the characteristics of the new cultivar. These attributes in combination distinguish 'MN 1369' as a new and unique cultivar of *Vitis*.

1. 'MN 1369' exhibits seedless berries (small seed traces only).
2. 'MN 1369' exhibits berries that are medium in size.
3. 'MN 1369' exhibits berries with a pleasant tropical fruit flavor.
4. 'MN 1369' exhibits loose berry clusters.
5. 'MN 1369' exhibits production of berries on secondary buds.
6. 'MN 1369' exhibits berries with adherent skin unless overripe.

The female parent plant of 'MN 1369' differs from 'MN 1369' in having berries that are smaller in size, seeds, a later harvest period, and a different flavor. The male parent plant of 'MN 1369' differs from 'MN 1369' in having berries that are red in color, smaller in size, have a more mild flavor, and borne on smaller grape clusters. 'MN 1369' can also be compared to the *Vitis* cultivars 'Louise Swenson' (not patented) and 'Somerset Seedless' (not patented). 'Louise Swenson' is similar to 'MN 1369' in being cold hardy and in having berries that are green in color. 'Louise Swenson' differs from 'MN 1369' in having berries that have seeds, slip skin, a light labrusca flavor, and in being used primarily as a wine grape. 'Somerset Seedless' is similar to 'MN 1369' in having berries that are seedless and have adherent skin. 'Somerset Seedless' differs from 'MN 1369' in having berries that are smaller and pink in color with a different flavor profile and borne on smaller clusters, and in having a less vigorous growth habit.

STATEMENT REGARDING PRIOR DISCLOSURES BY THE INVENTORS

The Applicants assert that no publications or advertisements relating to sales, offers for sale, or public distribution occurred more than one year prior to the effective filing date of this application. Any information about the claimed plant would have been obtained from a direct or indirect disclosure from the Inventor. The Applicants claim a prior art exemption under 35 U.S.C. 102(b)(1) for disclosures and/or sales that fall within a one-year grace period prior to the filing date. Disclosures include website listings by University of Wisconsin Fruit Program, HortScience (ASHS), ResearchGate, Acta Horticulturae, ICGBG, USDA, NIMSS, University of Wisconsin-Madison, University Digital Conservancy.

BRIEF DESCRIPTION OF THE DRAWINGS

The accompanying color photographs illustrate the overall appearance and distinct characteristics of the new grapevine. The photographs were taken of 14 year old plants of 'MN 1369' as grown under standard field conditions in Excelsior, Minnesota.

The photograph in FIG. 1 provides a view of the plant habit of 'MN 1369'.

Figure 1:
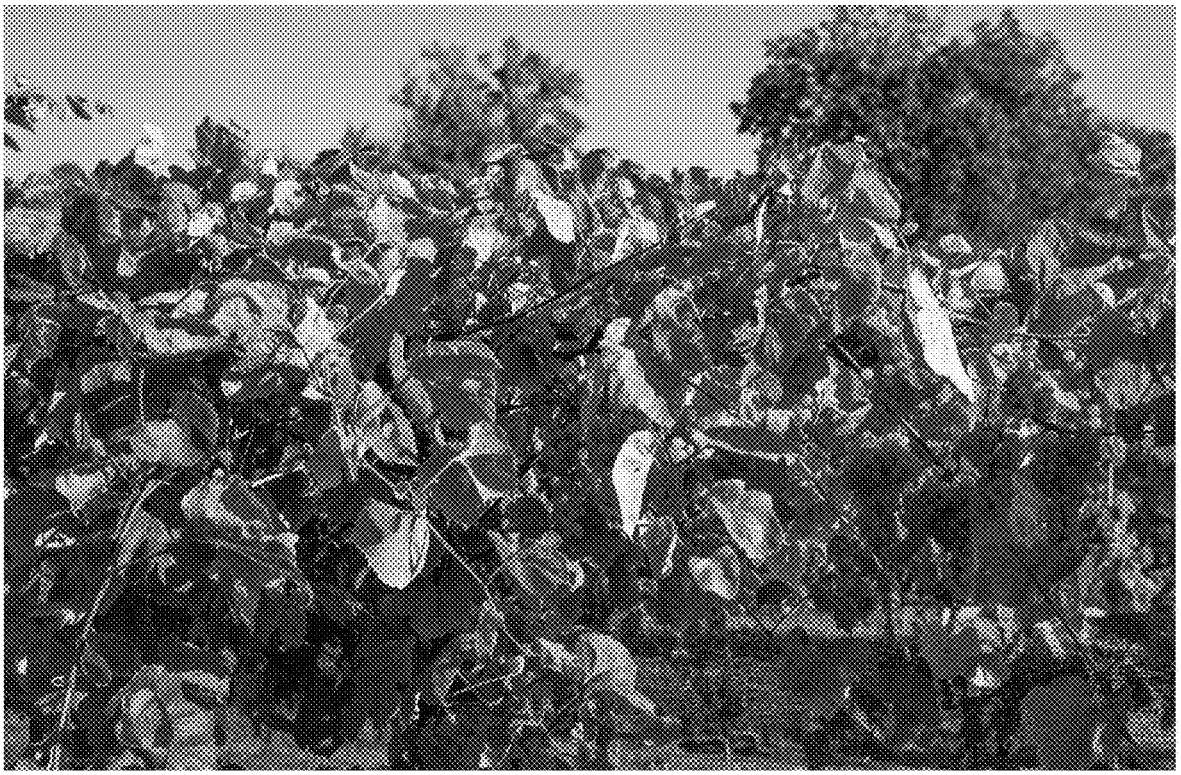
Figure 2:
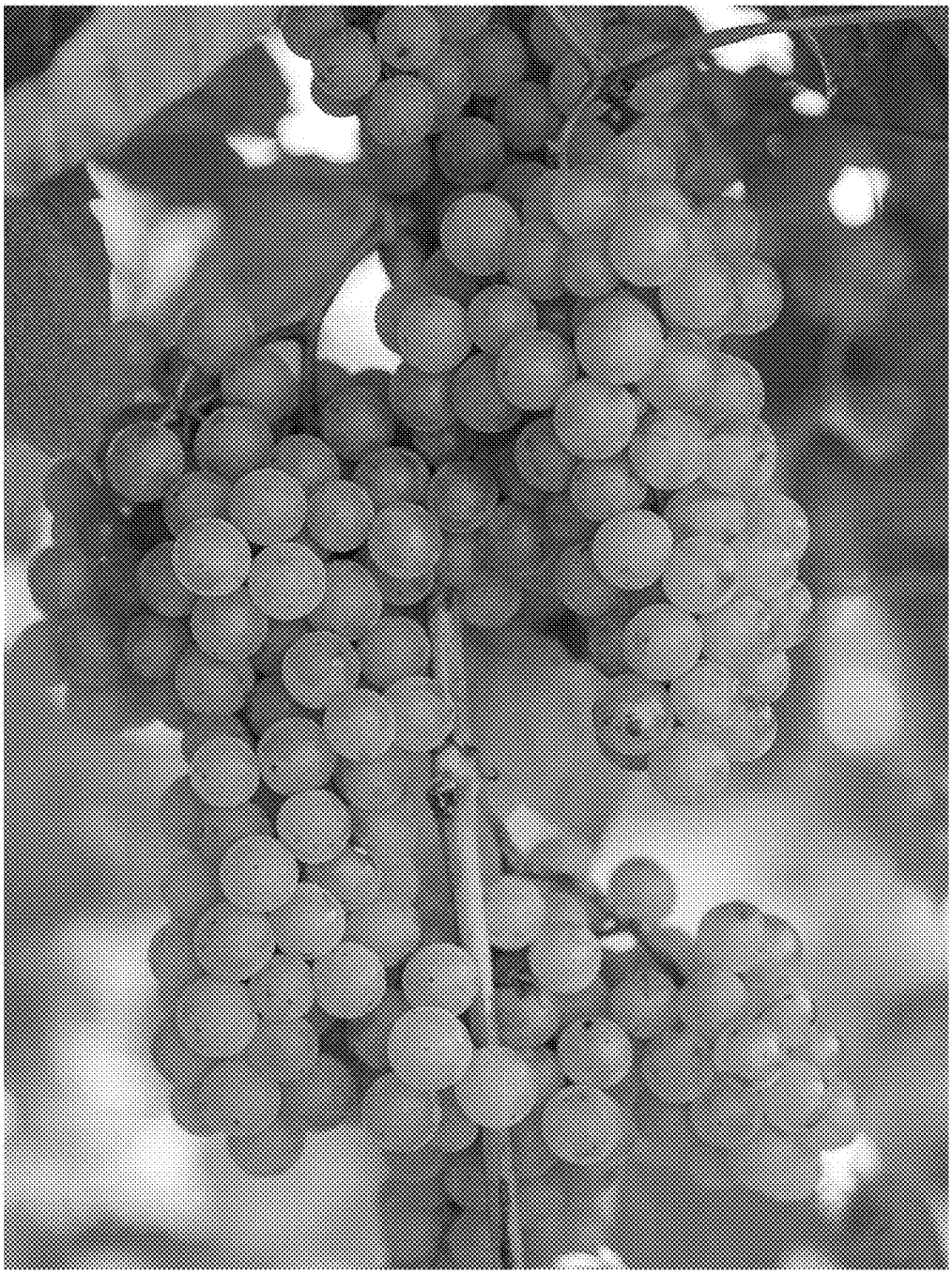

The photograph in FIG. 2 provides a close-up view of the berry clusters of 'MN 1369'.

The photographs depict color features as true as is reasonably possible with the digital photography methods used and the color values cited in the detailed botanical description accurately describe the new *Vitis*.

DETAILED BOTANICAL DESCRIPTION

The following traits have been repeatedly observed and represent the characteristics of the new cultivar. The measurements, observations and descriptions that follow describe a plant 15 years in age as grown outdoors in a trial vineyard in Excelsior, Minnesota. 'MN 1369' has not been observed under all possible environmental conditions and the phenotype may vary somewhat with variations in temperature, day length, light intensity, trellis system, pruning, pest control and other cultural practices without, however, any variance in the genotype. Many of the descriptors are based on those set forth by the International Board for Plant Genetic Resources in collaboration with the Organisation Internationale de la Vigne et du Vin (OIV) and the International Union for the Protection of New Varieties of Plants. All dimensions are given as means. The color determination is in accordance with The 2015 Colour Chart of The Royal Horticultural Society, London, England, except where general color terms of ordinary dictionary significance are used.

General description:

*Blooming period*.—Typically first two weeks of June in Excelsior, Minnesota.

*Plant type*.—Perennial fruit producing vine.

*Plant habit*.—Open and orderly.

*Height and spread*.—2.2 m in height, 2.7 m in spread.

*Propagation*.—Hardwood stem cuttings.

*Growth rate*.—Moderate.

*Time required for root development*.—Root initiation 2 to 3 weeks, a young rooted plant is produced within one year from a rooted cutting.

Mature canes:

*Color of canes*.—One-year-old canes; a blend of 175A, 165B and 166A, new canes; a blend of 144D, 178A, 166A and 174A.

*Length of canes*.—One-year-old canes; average of 1.8 m (prior to pruning).

*Diameter of canes*.—Average of 7.4 mm mid cane.

*Diameter at nodes*.—Average of 10.3 mm.

*Internode length*.—Average of 11.9 cm.

*Lenticels*.—None.

*Cane cross-section shape*.—Oval to round.

*Surface*.—Smooth with no hairs.

*Density of hairs on mature cane*.—None.

*Tendril pattern on shoot*.—2,0,2,0 etc. (two nodes with a tendril followed by one node without).

*Tendrils forked*.—Yes.

*Tendril texture*.—Glabrous.

*Tendril length*.—Average of 18.4 cm.

*Tendril color*.—Young and mature shoots; N144B.

*Bud width*.—4 mm.

*Bud length*.—6 mm.

*Bud shape*.—Triangular.

*Bud color*.—A blend of 165A and 165B.

*Bud burst*.—Medium.

Trunk:

*Bark texture*.—Rugose, matte, and exfoliating.

*Bark color*.—Striated, a blend of 198A, 197A, and 202C.

*Trunk shape*.—Oval.

*Trunk diameter*.—An average of 5.6 cm on diameter.

Mature leaves: Descriptors including the designations N1 through N5, relate to "OIV-Code Numbers 065-093" of *Preliminary Minimal Descriptor List for Grapevine Varieties* (Dettweiler E., 1991, Institüt fur Rebenzüchtung, Geilweilerhof, Germany).

*Length of blade*.—12.5 cm.

*Width of blade*.—16.6 cm.

*Shape of blade*.—Fig-like.

*Number of lobes*.—5.

*Blade margins*.—Incised into lobes with lobes moderately to deeply serrated.

*Length of primary (midrib) vein N1 from the tip of the blade to the petiole sinus*.—13 cm.

*Length of petiole compared to length of middle vein (midrib)*.—Middle vein is 3 cm longer than length of petiole.

*Length of vein N2 from the tip of the first major lobe of the blade to the petiole sinus*.—10.7 cm.

*Length of vein N3 from the tip of the second major lobe of the blade to the petiole sinus*.—7.7 cm.

*Length of vein N4 from the tip of the third major lobe of the blade to where it joins the vein measured in N3*.—4.8 cm.

*Length of vein N5 from the tip of the first tooth proximal to the petiole sinus to where it joins the vein measured in N4*.—1.7 cm.

*Leaf vein anthocyanin*.—None.

*Length of N2 teeth*.—Up to 0.5 cm.

*Width of N2 teeth*.—Up to 1 cm.

*Length/width ratio of N2 teeth*.—0.5 cm.

*Length of N4 teeth*.—Up to 0.5 cm.

*Width of N4 teeth*.—Up to 1.5 cm.

*Length/width ratio of N4 teeth*.—0.75 cm.

*Shape of teeth*.—Convex.

*Arrangement of petiolar sinus*.—Open.

*Shape of petiolar sinus*.—Open.

*Shape of base of petiolar sinus*.—Lyre-shaped.

*Depth of petiolar sinus*.—3.5 cm.

*Width of petiolar sinus*.—3.1 cm.

*Petiole*.—9.1 cm in length, 2.9 mm in width, 144C in color and suffused with 183D on sun exposed side.

*Shape of upper sinuses*.—Urn-shaped.

*Shape of base of upper sinuses*.—Rounded.
*Arrangement of upper sinuses*.—Wide open.
*Glossiness of adaxial and abaxial surface*.—Adaxial surface is glossy and abaxial surface is not and has low density of small, intervenal trichomes.
*Pubescence on adaxial surface*.—None.
*Pubescence on abaxial surface*.—Very minute erect hairs on veins.
*Blistering on adaxial surface*.—None.
*Color of adaxial leaf surface*.—137B, veins 146C.
*Color of abaxial leaf surface*.—139C, veins 146C.
*Color of leaf petiole*.—144C blend of 183D and 175A.
*Center lobe size*.—6 cm in length, 4 cm in width.
*Lateral lobe size*.—4 cm in length and width.
*Basal lobe size*.—4 cm in length and width.
*Density of foliage*.—Moderate.

Young shoots:
*Form of shoot tip*.—Mainly open.
*Density of prostate hairs on tip*.—Moderately pubescent.
*Anthocyanin coloration of the prostrate hairs on tip*.—Absent or very weak.
*Density of erect hairs on tip*.—None observed.
*Petiole pigmentation*.—A blend of 145A and 144C, striated and suffused with 183A, 183B on sun exposed side.
*Shoot attitude*.—Semi-erect.
*Shoot pigmentation* (*internodes and nodes*).—A blend of 145A and 144C, striated and suffused with 183A, 183B on sun exposed side.
*Young leaves*.—138A in color on upper surface, 144B on lower surface, upper and lower surface matte, veins match surface colors.

Flowers:
*Fragrance*.—Moderately fragrant.
*Mean time of flowering*.—Second week of June when grown in Excelsior, MN.
*Color of calyx*.—144A.
*Flowering shoot vigor*.—Vigorous.
*Flowering shoot attitude*.—Semi-erect to erect.
*Sepal number*.—5, sepals fused into continuous calyx.
*Calyx shape*.—Ring-shaped.
*Calyx size*.—0.5 mm in length, 2 mm in width.
*Calyx apex*.—Fused to ovary.
*Calyx base*.—Fused to pedicel.
*Nectary*.—1.5 mm in diameter, 0.5 mm in length, 145A in color.
*Calyx surface*.—Glabrous.
*Petals*.—5, fused in calyptra cohering at summit; 1.8 mm in width and 1 mm in depth, reflexed after dehiscence, 144A in color, margins 155B in color.
*Number of flowers/cluster*.—Average of 150.
*No. of clusters per cane*.—Average of 2.
*Flower buds*.—5 mm in length, 2 mm in width, 144B in color, obovate in shape, glabrous and slightly glossy surface.
*Size of individual entire flower*.—5 mm in length, 1.1 cm in width (to end of stamens).
*Pollen fertility*.—Fertile based on use in controlled crosses.
*Reproductive organs*.—Fully developed stamens and fully developed gynoecium.
*Color of stamen*.—Anther; 15A, fading to 158B, filament; NN155D.
*Stamen number*.—Average of 5.
*Filament length*.—Average of 6 mm.
*Anther*.—1 mm in length and diameter, basifixed.
*Pollen quantitity and color*.—Abundant and 15A in color.
*Pistil*.—1, ovary; 1 mm in length, 1 mm in width at base, urn-shaped, glabrous surface, color 143A, stigma; 1 mm in width, <1 mm in length, N144A in color.
*Pedicel*.—6 mm in length, 0.5 mm in width, 145A in color, surface is glossy and glabrous.
*Peduncle*.—7 mm in length, 2 mm in width, 145A in color, surface is glossy and very sparsely covered with woolly pubescence.
*Position of first flowering and fruiting node*.—Typically node 3.

Fruit:
*Cluster length*.—Average of 13.8 cm (ranges from 10 to 16.5 cm).
*Cluster shoulders*.—Typically 1.
*Cluster diameter*.—Average of 11.4 cm (ranges from 9 to 20 cm).
*Cluster weight*.—155.4 g (ranges from 73.8 to 224.5 g).
*Cluster density*.—Medium to very dense, average of 114 berries per cluster.
*Berry weight*.—1.9 g (ranges from 1.5 to 2.2 g).
*Berry length*.—Average of 1.5 cm.
*Berry diameter at equator*.—Average of 1.4 cm.
*Berry shape*.—Round.
*Berry cross-section*.—Circular.
*Berry, color of skin*.—At maturity; 153A and 153B.
*Berry, color of flesh*.—A blend of 152C and 152A very weak or no anthyocyanin presence.
*Berry firmness*.—Slightly firm.
*Berry skin thickness*.—Medium to thin.
*Berry skin bloom* (*cuticular wax*).—Low.
*Berry size uniformity*.—Medium.
*Berry, particular flavor*.—Tropical fruit flavor and aromatic.
*Length of pedicel*.—Average of 8.8 mm.
*Pedicel diameter*.—Average of 1.4 mm.
*Pedicel color*.—A blend of 146D and 146B with 176C throughout.
*Peduncle* (*rachis*).—An average of 4 cm in length and 3.8 mm in width (mid point), a blend of 146D and 148B with some anthocyanin shading of 178B.
*Berry, separation from pedicel*.—Easy.
*Berry, presence of seeds*.—Only small seed traces, nearly seedless.
*Seed number/berry*.—3.
*Seed length*.—5.2 mm.
*Seed width*.—2.5 mm.
*Seed length/width ratio*.—2.24.
*Seed weight*.—0.0047 g (dry) or 0.0078 g (fresh).
*Seed color*.—A blend of 200C and 166D with 167A on the ends.

Fruit chemistry and harvest: Values represent the means (with ranges in parentheses) for fruit harvested over three growing seasons 2019-2022.
*Harvest date*.—Mid-August through beginning of September in Excelsior, Minnesota.
*Time of beginning berry ripening*.—Second to third week of July.
*Soluble solids content*.—20.6 degree Brix (18 to 23.6).
*pH*.—2.98 (2.90 to 3.04).
*Titratable acidity*.—9.75 g/L (7.30 to 12.48).

*Berry use*.—Table grapes (fresh food market).

*Berry storage*.—Clusters were stored in commercial packing (clear plastic, vented polyethylene bags) and place in cardboard boxes lines with a standard microperforated poly liner (1%), absorbent pad (under bags of clusters), and slow release SO2-generating pad containing 73.5% Na2S2O5 (on top of clusters), boxes were stored at 2.2 degrees C., stored up to 6 weeks with acceptable overall appearance, splitting, and decay and 4 weeks before rachis browning was below a consumer threshold.

Vineyard performance: Based on observations compiled over five years (2019-2023).

*Susceptibility to powdery mildew* (*Erysiphe necator*).—Low to moderate.

*Susceptibility to downy mildew* (*Plasmopara viticola*).—Low.

*Susceptibility to black rot* (*Guignardia bidwellii*).—Low to none.

*Susceptibility to grey mold* (*Botrytis cinerea*).—None.

*Susceptibility to foliar phylloxera* (*Daktulosphaira vitifoliae*).—None.

*Susceptibility to crown gall* (*Agrobacterium tumefaciens*).—None.

*Susceptibility to phenoxy herbicide drift* (*e.g.,* 2,4-*D*) .—Low.

*Berry splitting*.—Low to medium.

*Berry shelling*.—Low to medium.

*Vigor level*.—Medium.

*Cold hardiness*.—At least in USDA Zone 4.

*Wood ripening*.—Moderate.

It is claimed:

1. A new and distinct variety of grapevine plant named 'MN 1369' as described and illustrated herein.

* * * * *